Feb. 12, 1974 B. S. JURALE Plant Pat. 3,475
APPLE TREE
Filed June 15, 1972
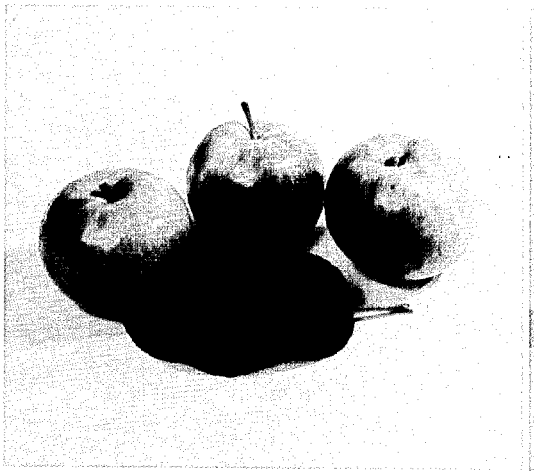
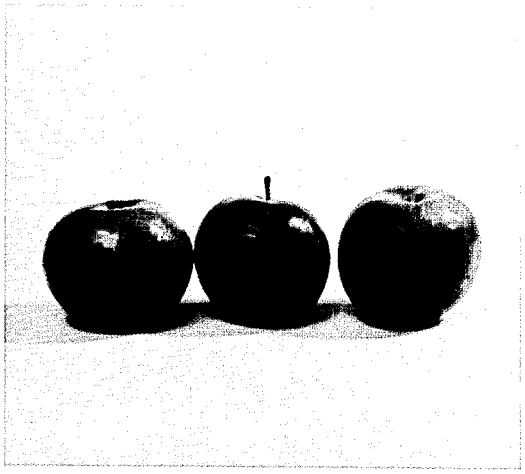
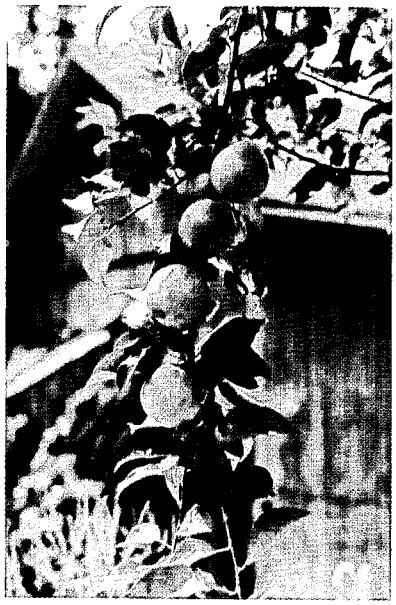
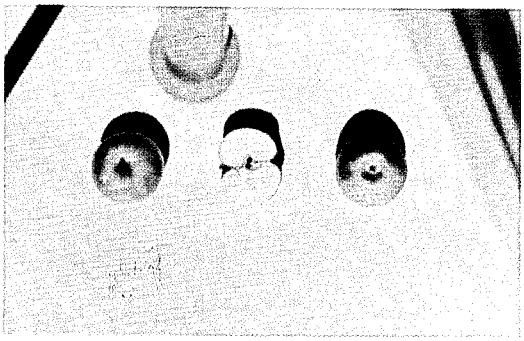
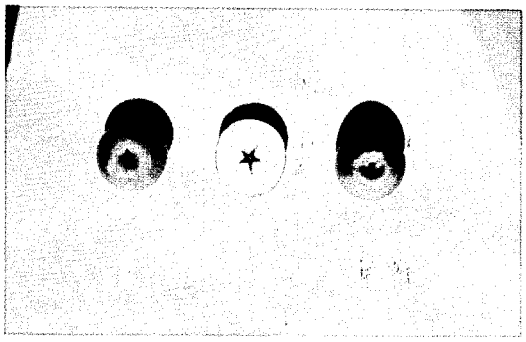

United States Patent Office

Plant Pat. 3,475
Patented Feb. 12, 1974

3,475

APPLE TREE

Bernard S. Jurale, 457 New Hanover Ave., South Meriden, Conn. 06450

Filed June 15, 1972, Ser. No. 263,274
Int. Cl. A01h *5/03*
U.S. Cl. Plt.—34 1 Claim

The present invention relates to a new and distinct variety of apple tree discovered on my property in Meriden, Conn. At the time I discovered this tree, it had borne its first fruit. The appearance, tartness and aroma of the fruit indicated that the tree had grown from a seed of a nearby Baldwin tree, which had been pollenated by a Red Astrachan tree next to it and produced an apple resembling the Red Astrachan in coloring, form, size and thin skin with the Baldwin influence accounting for its vigorous growth, later maturing fruit, keeping qualities, spicy taste and unique aroma. The tree is normal in size and shape and blossoms profusely, but earlier than any of the standard varieties of apple.

The apple is excellent for eating and for pie, applesauce and cider. The juice, when freshly expressed has a pH of 2.7 to 3.0 when hard ripe, producing a tartness which, however, is balanced by a high sugar content. Apples from this tree and from trees, which I have since asexually reproduced by grafting, are exceptionally digestible and can be eaten by people who cannot tolerate the bland apple varieties. The juice from apples which have been frozen and then thawed has a very delicate and pleasing flavor, which oddly enough is unlike the flavor usually associated with apples. Fermentation of the nectar produces a champagne-like wine. As testimony of the distinctive and usual taste and flavor of the juice and cider made from these apples, expert orchardists who know and have tried apple juice and cider from many varieties of apples are unable to identify the juice of frozen apples from my new tree as having been made from apples. Thinnings picked about one month before the fruit is ripe make excellent cider when processed in this manner.

In the years since the aforesaid tree first bore fruit, I have propagated it through asexual reproduction by grafting onto a number of different rootstocks in my orchard. The fruit from the grafted trees confirms that the hereinabove-mentioned characteristics come true and are established and transmitted through succeeding propagations. While the coloring of the fruit varies somewhat depending on the rootstock onto which the graft is made, the distinctive combination of characteristics referred to herein are found in the fruit of trees propagated from the parent tree and of succeeding propagations, without diminishing its unique qualities of flavor, aroma and texture.

The accompanying drawing shows typical specimens of the fruit of my new variety. One view shows the fruit in cross section both along the axis and perpendicular thereto, in order to expose the interior details, and another view shows three specimens of the fruit in top perspective, with a leaf of my new variety, while a third view shows a cluster of apples as they appear on the tree, all depicted in color as nearly true as it is reasonably possible to make a color photograph. The exposure of the fruit to the sun enhances the amount of intensity of the color but the color has no effect on the flavor and aroma.

The following detailed description of my new variety of apple tree employs color terminology in accordance with ordinary dictionary significance:

Locality where grown and observed: Meriden, New Haven County, Conn.

Tree: Medium large; very vigorous; hardy; balanced spread and height; fast growing; very productive; regular bearer.

*Trunk.*—Medium stockiness; predominantly smooth.

*Branches.*—Medium thickness; smooth; well balanced.

*Color.*—Light grey (color plate Webster's Internat. Dict., 2nd Ed., Unabridged, 1943).

*Lenticels.*—Few; small.

*Leaves.*—Large size with blade up to 5 inches long and 3 inches wide. Ovate but with pronounced acuminate tip; acute base; rugose. Margin serrated but serrations are more rounded than pointed. Petiole—long, often 2 inches; medium thickness. Color—Brunswick Green (Webster's Internat. Dict., 2nd Ed., unabridged, 1943).

Flowers: Early as compared to other varieties; medium large.

*Color.*—White with bloom wanting. Pink, May 2 to May 6, and full bloom, May 9 and 10 in 1970.

Fruit:

*Maturity when described.*—Hard ripe about Sept. 1,

*Size.*—Medium to large. Not uniform. Ratio of average overall axial diameter to average overall transverse diameter is 1 to about 1.25 or 1.5. Average transverse diameter—about 2½ inches to about 3 inches when hard ripe.

*Form.*—Oblate at both base and apex.

*Cavity.*—Symmetrical.—from acute to acuminate. Depth—about ½ inch. Breadth—about 1 inch. Markings: Color—dark greenish yellow.

*Basin.*—Symmetrical; rounded. Depth—about ¼ inch. Breadth—about 1 inch.

*Stem.*—Variable in length and thickness.

*Calyx.*—Closed, segments persistent and pubescent.

*Skin.*—Thin, resilient, smooth. Dots—conspicuous; many; variable in size, widely scattered. Color—yellowish green. Ground color—yellow—green with variable carmine areas and streaks.

*Flesh.*—Not juicy. Color—satiny white. Texture—firm; crisp. Flavor—tart due to high acidity yet sweet due to high sugar content. Very aromatic and spicy. Quality—unlike any other variety. Excellent taste.

*Core.*—Bundle area—very small; symmetrical. Halves of core—unequal; occupies very small space along the axis and is equally spaced from the inner ends of both the base and the apex: Case of core—distinct and firm.

Seeds:

*Number.*—Usually about 8 to 10, one or two per cell, usually two.

*Form.*—Acute.

*Size.*—5/16 inch by 3/16 inch.

*Color.*—Chestnut brown.

Use: Market; dessert; culinary; cider and apple champagne. Keeping quality: Excellent. Peak quality occurs when hard ripe. Tartness diminishes slightly with storage. Good quality is preserved for 120 days under normal storage conditions.

I claim:

1. A new and distinct variety of apple tree, substantially as herein shown and described, characterized particularly as to novelty by the distinctive flavor of the fruit, which is enhanced by its high pH and tartness and by its high sugar content, as well as by the unusual flavor the cider made from said fruit which has been frozen, said fruit resembling the Red Astrachan in color, form and tenderness, but having the late maturing and keeping qualities, as well as spicy taste and aroma of the Baldwin.

No reference cited.

ROBERT E. BAGWILL, Primary Examiner